United States Patent [19]

Wiegand et al.

[11] Patent Number: 5,437,179
[45] Date of Patent: Aug. 1, 1995

[54] FAST GAS CHROMATOGRAPHY METHOD, APPARATUS AND APPLICATIONS

[75] Inventors: Patrick M. Wiegand, South Charleston; John F. Fisher, St. Albans; John R. Parris, Cross Lanes; Elizabeth S. Ballard, Charleston; Courtland P. Sears, III, Dunbar; George W. Schwarz, Jr.; Cloid R. Smith, III, both of Charleston, all of W. Va.

[73] Assignee: Union Carbide Chemicals & Plastics Technology Corporation, Danbury, Conn.

[21] Appl. No.: 88,677

[22] Filed: Jul. 7, 1993

[51] Int. Cl.$^6$ .............................................. G01N 30/20
[52] U.S. Cl. .................................. 73/23.35; 73/23.42
[58] Field of Search ................... 73/23.35, 23.36, 23.4, 73/23.42; 95/83, 87; 96/101, 105

[56] References Cited

U.S. PATENT DOCUMENTS

| | | | |
|---|---|---|---|
| 4,726,822 | 2/1988 | Cates et al. | 55/267 |
| 4,923,486 | 5/1990 | Rubey | 55/67 |
| 5,028,243 | 7/1991 | Rubey | 55/67 |
| 5,096,471 | 3/1992 | Sacks et al. | 55/67 |
| 5,099,743 | 3/1992 | Rounbehler et al. | 86/50 |

OTHER PUBLICATIONS

Tijssen R., et al. "Theoretical Aspects...", Anal Chem 59, 1007–1015, 1987.
Sandra, P., "Fast Capillary..." LC/GC 5, 236–246, 1987.
Lee et al. "Recent Developments...", American Laboratory, 111–119, 1989.
Peters et al. "Instrumentation and Strategies..." Analyst, 116, 1313–1320, 1991.
Desty, D. H. "Advances in Chromatography," 1., 199–277, (1965).
Gaspar, G., Annino, R., Vidal-Madjar, C., Gulochon, G., "Influence of Instrumental Contributions on the Apparent Column Efficiency in High Speed Gas Chromatography," Anal Chem. 50, 1512–1518,(1978).
Schutjes, C. P. M., Vermeer, E. A., Rijks, J. A. Cramers, C. A., "Increased Speed of Analysis in Isothermal and Temperature-Programmed Capillary Gas Chromatography" by Reduction of the Column Inner Diameter, Journal of Chromatography, 253, 1–16, (1982).
Gaspar, G., Vidal-Madjar, C. Gulochon, G., "Fast Analysis by Gas Chromatography," Chromatgraphia, 15, 125–132, (1982).
Schutjes, C. P. M., Cramers, C. A., Vidal-Madjar, C., Guiochon, G., "Fast 'Fluidic Logic' Injection at Pressures up to 25 Bar in High-Speed Capillary Gas Chromatography," Journal of Chromatography, 279, 269–277,(1983).
Onuska, F. I., "Narrow-Bore Wall-Coated Open-Tubular Columns for Fast High-Resolution Gas Chromatographic Separations of Toxicants of Environmental Concern," Journal of Chromatography, 289, 207–221, (1984).
Phillips, J. B., Luu, D., Pawliszyn, J. B., Carle, G. C., "Multiplex Gas Chromatography by Thermal Modulation of a Fused Silica Capillary Column," Anal Chem. 57, 2779–2787, (1985).
Ewels, B. A., Sacks, R. D., "Electrically-Heated Cold Trap Inlet System for High-Speed Gas Chromatography," Anal Chem. 57, 2774–2779, (1985).

(List continued on next page.)

Primary Examiner—Hezron E. Williams
Assistant Examiner—Michael J. Brock
Attorney, Agent, or Firm—S. H. Hegedus

[57] ABSTRACT

The present invention is directed to methods and apparatus for conducting gas chromatography more rapidly than previously disclosed. By means of the present invention the time necessary to conduct a gas chromatographic analysis can be reduced by more than 50%. The methods and apparatus employed reduce system dead volumes to prevent band broadening and mixing of the sample components as the gas sample is analyzed. The present invention also relates to the apparatus described above as applied to controlling chemical, refining, and other processes.

7 Claims, 12 Drawing Sheets

OTHER PUBLICATIONS

Lomovzceva, T. I., Milinskaya, I. N., Myagkov, E. A., Pogosbekyan, G. V., Romanov, N. A., Filatova, Z. I., Usfin, V. S., "Chromatographic Method for High-Speed Analysis of Gas Components," *Journal of Chromatography*, 365, 459–461, (1986).

Van Es, A., Janssen, J., Bally, R. Cramers, C., Rijks, J., "Sample Introduction in High Speed Capillary Gas Chromatography; Input Band Width and Detection Limits," *Journal of High Resolution of High Resoluation Chromatography & Chromatography Communications*, 10, 273–279, 1987.

Tijssen, R., Van den Hoed, N., Van Kreveld, M. E., "Theoretical Aspects and Practical Potentials of Rapid Gas Analysis in Capillary Gas Chromatography," *Anal Chem.*, 59, 1007–1015 (1987).

Sandra, P., "Fast Capillary Gas Chromatography," *LC/GC*, 5, 236–246, (1987).

Lanning, L. A., Sacks, R. D., Mouradian, R. F., Levine, S. P., Foulke, J. A., "Electrically Heated Cold Trap Inlet System for Computer-Controlled High-Speed Gas Chromatography," *Anal Chem.* 60, 1994–1996, (1988).

Van Es, A., Cramers, C., Rijks, J., "Detection Limits of Thermal Conductivity and Photoionization Detectors in High Speed Narrow Bore CGC," *Journal of High Resolution Chromatography*, 12, 303–307, (1989).

Lee, G., Ray, C., Siemers, R., Moore, R., "Recent Developments in High Speed Gas Chromatography," *American Laboratory*, 111–119, (1989).

Pedersen, N. H., Jorgensen, S. B., "Gas Chromatographic Subsystem for Fast On-Line Concentration Profile Measurements for Advanced Distillation Column Control," *Analytica Chimica Acta*, 238, 139–148, (1990).

Mouradian, R. F., Levine, S. P., Sacks, R. D., "Evaluation of a Nitrogen-Cooled Electrically Heated Cold Trap Inlet for High-Speed Gas Chromatography," *Journal of Chromatographic Science*, 28, 643–648, (1990).

Rankin, C., Sacks, R., "Computer-Controlled Vacuum Backflush for Capillary GC," *Journal of High Resolution Chromatography*, 13, 674–678, (1990).

Klemp, M., Sacks, R., "Vacuum Backflush-Recycle System for GC Analysis of High-Purity Solvents," *Journal of Chromatographic Science*, 29, 114–121, (1991).

Klemp, M., Sacks, R., "Sample Decomposition in an Electrically-Heated Cold-Trap Inlet System for High-Speed Gas Chromatography," *Journal of High Resolution Chromatography*, 14, 235–240, (1991).

Rubey, W. A., "A Different Operational Mode for Addressing the General Elution Problem in Rapid Analysis Gas Chromatography", *Journal of High Resolution Chromatography*, 14, 542–547, (1991).

Peters, A., Klemp, M., Puig, L., Rankin, C., Sacks, R., "Instrumentation and Strategies for High-Speed Gas Chromatography," *Anayst*, 116, 1313–1320, (1991).

Peters, A., Sacks, R., "High-Speed GC Analysis for Low-Molecular-Weight Carbon-Hydrogen and Carbon-Hydrogen-Chlorine Compounds with Porous-Layer Open-Tubular Columns," *Journal of Chromatographic Science*, 29, 403–409, (1991).

Rankin, C., Sacks, R., "A Computer-Controlled, High-Speed, Repetitive Gas Chromatography System," *LC/GC*, 9, 428–434 (1991).

Klemp, M. A., Sacks, R. D., "Hold-up Time Measurements for High-Speed Gas Chromatography," *Journal of Chromatographic Science*, 29, 507–510, (1991).

Klemp, M., Sacks, R., "Strategies for Rapid GC Impurity Analysis of High-Purity Solvents I: Instrumentation and Procedures," *Journal of Chromatographic Science*, 29, 243–247, (1991).

Klemp, M., Sakcs, R., "Strategies for Rapid GC Impurity Analysis of High-Purity Solvents II: Column Selcection and Solvent Effects," *Journal of Chromatographic Science*, 29, 248–252, (1991).

Peters, A., Sacks, R., "Inlet Pressure Programming for High-Speed Gas Chromatography," *Journal of Chromatographic Science*, 30, 187–191, (1992).

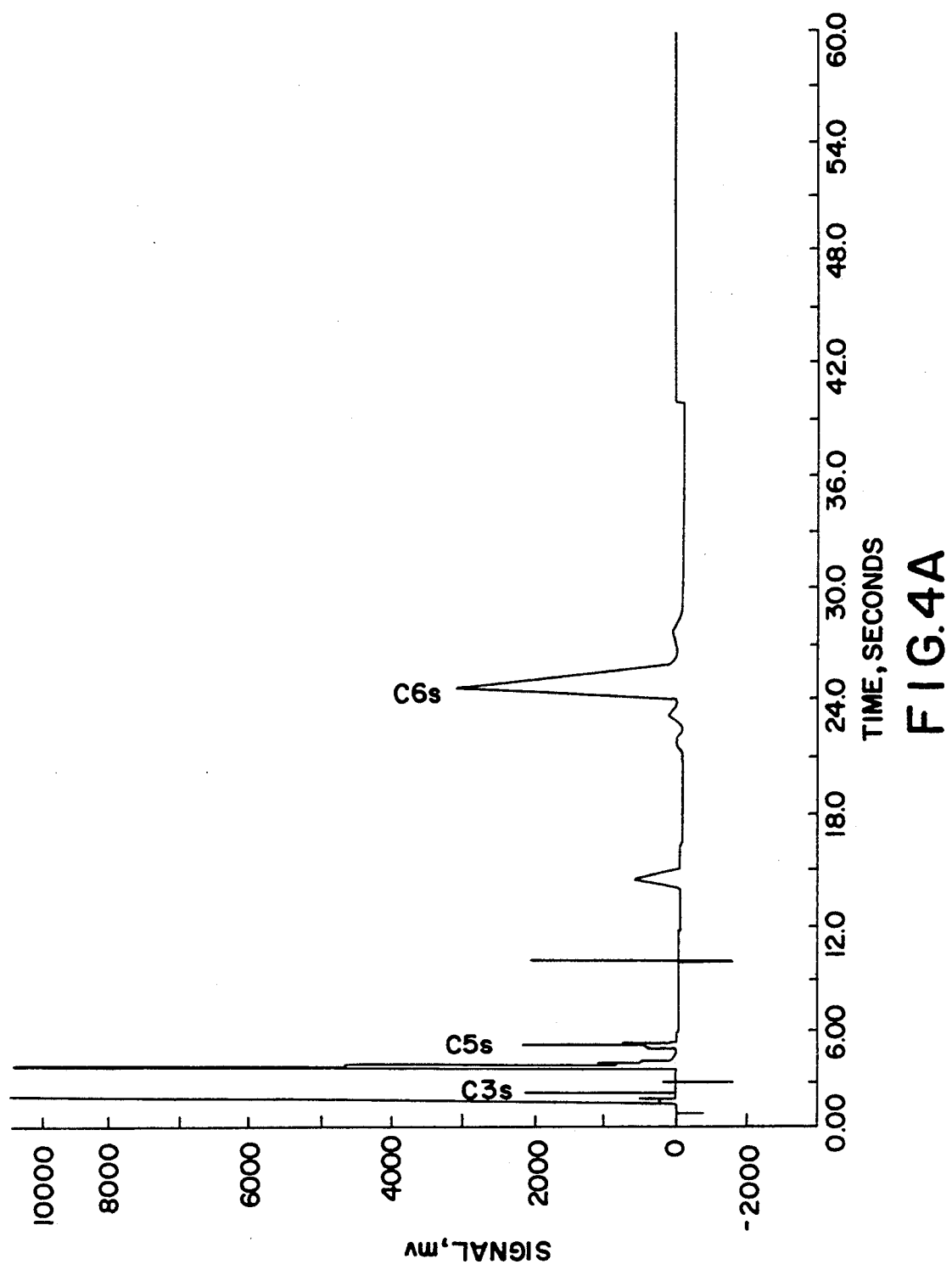

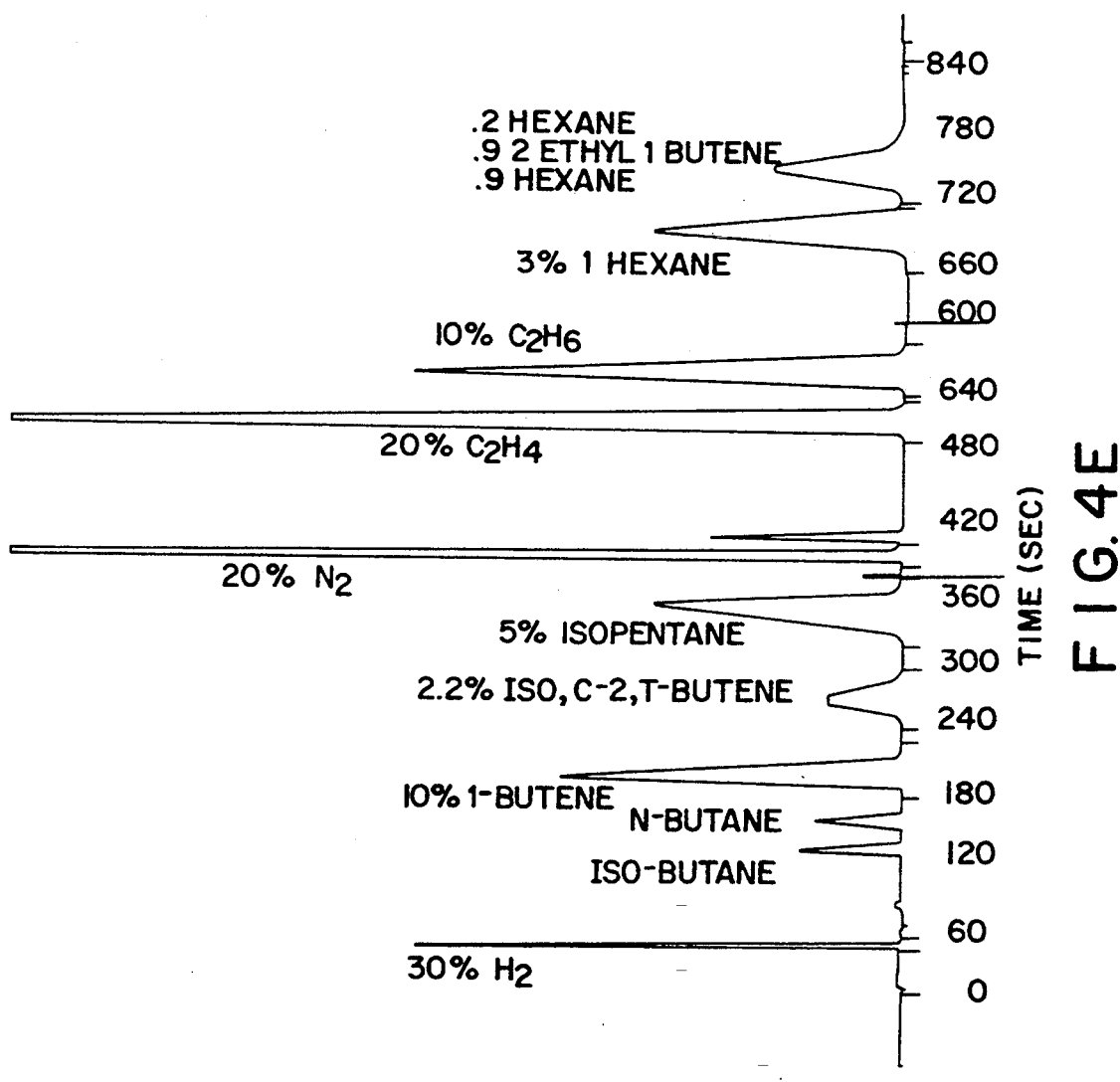

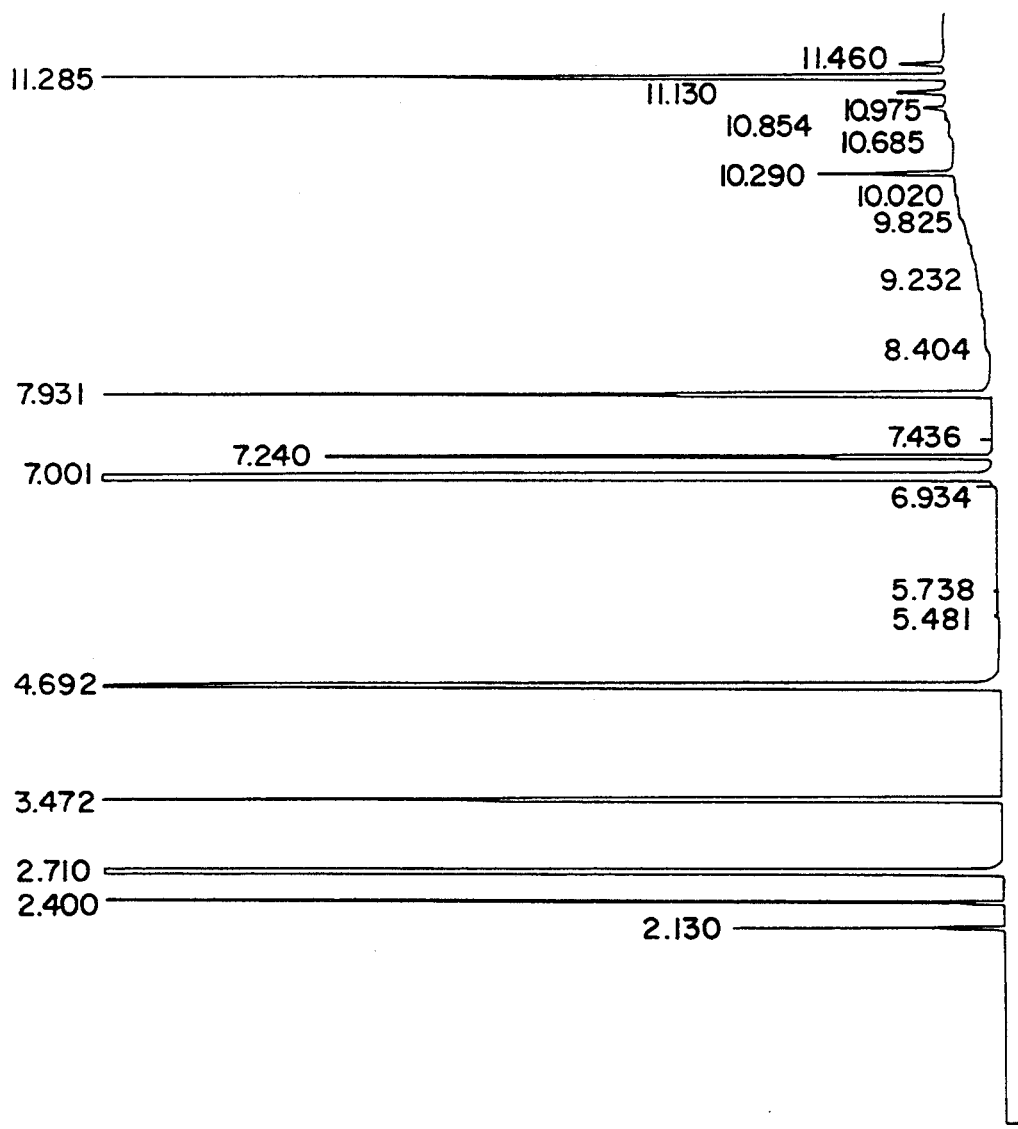

FAST GAS CHROMATOGRAPHY METHOD, APPARATUS AND APPLICATIONS

FIELD OF THE INVENTION

This invention relates to apparatus and methods for conducting gas chromatography. More particularly, this invention relates to apparatus and methods which decrease the time necessary to conduct the analysis and the application of this technology to control chemical, refining and other processes.

BACKGROUND OF THE INVENTION

Gas chromatography (GC) is a widely employed technique used for the separation and analysis of mixtures of volatile and semi-volatile organic and inorganic mixtures. The mixture is separated into its components by eluting them from a column by means of a moving gas. The moving gas flows through the chromatographic column in which the various components separate from one another depending on their vapor pressures and interactions with the stationary phase within the chromatographic column. The stationary phase is commonly a thin layer of a nonvolatile liquid or an adsorbent solid. The concentration of the various eluted components are then measured via a detector at the end of the column. The detector generates an electrical signal, which in conjunction with appropriate electronics, produces peaks at various times. Proper analysis of the peaks allows one with skill in the art to determine both the identity and amount of the components in the sample.

Although gas chromatography is widely used today and provides excellent performance, efforts are continuing to optimize the performance of gas chromatographs. Along these lines efforts have been made to reduce the time necessary to complete gas chromatographic analyses. Usually the detection step is quite rapid, with the analysis time determined by the efficiencies of the separation column and the sample inlet system.

The commercial availability of high efficiency open-tubular capillary columns for GC has made possible very high resolution separations by using very long columns with very small inner diameters, Danddeneau, R. D., and Zerenner, E. H., *High Resolution Chromatography & Chromatography Communications,* 2, 351–356 (1979).

U.S. Pat. No. 5,096,471 (Sacks et al.) discloses the use of a vacuum pump in order to reduce the time necessary to perform the analysis. The vacuum pump causes backflushing of a short column after components of interest have been eluted, but before higher boiling components have been eluted thereby shortening the time required for analysis.

U.S. Pat. No. 4,923,486 (Rubey) discloses a time-programmable curvilinearly shaped negative temperature gradient along the length of the chromatographic column. The gas phase sample traveling along the column always passes to a column zone having a lower temperature than the previous column zone, thereby compressing sample bandwidths upon elution. The patent alleges a reduction in separation times when compared to conventional isothermal or temperature programmed gas chromatography.

Despite the disclosures of the prior art, there is a continuous desire to reduce the time necessary to conduct gas chromatography. Ideally, gas chromatographic analyses could be conducted very rapidly so that sample concentrations could be detected in desirable time frames. The rapid determination of sample components could then be used to better control various processes such as reactors, distillation columns, pressure swing absorption, absorptive and extraction processes and the like.

SUMMARY OF THE INVENTION

By virtue of the present invention, methods and apparatus are provided which are capable of performing gas chromatographic measurements more quickly than previously performed. The results are available in a much shorter time period, typically 50% of the time previously required, generally in less than 33% and sometimes results are obtained in 10% of the time previously required by traditional gas chromatographic techniques. The methods and apparatus of the present invention are not limited by the types of samples which are analyzed. Those with skill in the art will readily appreciate the use of the present invention for the many applications for which gas chromatography is currently employed.

The methods and apparatus of the invention reduce the time necessary to perform gas chromatography by minimizing system dead volume along with sample and component bandwidths. The apparatus employs low dead volume fittings on the connections between the various components of the apparatus in order to minimize band broadening. In addition, various components such as the injector and detector have been selected or modified to operate at high rates of speed and to prevent mixing of the sample components in the apparatus. The data acquisition system, including the computer, software, and processing apparatus also operates at high speeds. These modifications will be discussed in greater detail throughout the specification.

As used herein in this application "repetitive" means multiple samples are analyzed without the intervention of a human being to perform such tasks such as to select a sample, to inject the sample into the apparatus and reinitiate the process.

Accordingly, in one aspect, the present invention is directed to a method for conducting repetitive gas chromatography which comprises:
 a) providing a controlled flow of carder gas;
 b) providing a sample selection mechanism;
 c) providing a sample injection mechanism;
 d) selecting the desired sample;
 e) injecting a sample of gas to be analyzed such that the plug flow time of the gas sample is less than 50 milliseconds;
 f) separating the components of the gas sample by gas chromatography;
 g) detecting the component concentrations of said gas sample thereby creating an electrical signal;
 h) amplifying and digitizing the signal from said detector;
 i) converting the digitized signal into component concentrations at the rate of at least 500 points per second; and
 j) providing a means for reinitiating the analysis process.

The method of the present invention is conducted through the use of an apparatus which is comprised of:
 a) at least one gas chromatography column capable of separating components in a gas sample, having a sample inlet port located at an upstream portion of said column and a sample elution port at an outlet of said column;

b) means for selecting a sample to be analyzed;
c) means for rapidly injecting into said chromatographic column a gas mixture that has a plug flow time of less than about 50 milliseconds;
d) means for detecting said separated gas components from the outlet of the column and creating an electrical signal;
e) means for converting said electrical voltage to a digital signal at a rate of greater than 500 points per second;
f) means for identifying sample components and calculating sample component levels from said digital signal;
g) means for transferring said sample component identification and sample component level information to a process control computer; and
h) means for reiterating the analysis.

The method and apparatus of the present invention can be conducted isothermally. In a preferred embodiment, the invention employs a novel temperature programming apparatus. The apparatus comprises:

a) at least one open tubular chromatographic column having a sample inlet located at an upstream portion of said column and a sample elution port at an outlet of said column;
b) a means to control the transfer of heat to said column for imparting a desired temperature change to said column, comprising:
  i) a conduit with an inlet orifice providing an inlet for a heat transfer fluid;
  ii) an annular opening within the conduit providing continuity with said inlet orifice providing a passage for said heat transfer fluid;
  iii) at least one heating means within said annular opening;
  iv) means to provide an electrical current to said heating means thereby imparting a temperature change to the heat transfer fluid; and
  v) outlet for said conduit and heat transfer fluid.

Additional timer and temperature controllers, programmers and heat transfer fluids may also be provided to the temperature control/column apparatus to modify the temperature of the column and its contents.

Due to the low mass and relatively high surface area (when compared with the mass) provided by the heating means, the heating means is able to undergo many heating and cooling cycles within a short period of time, which makes this apparatus particularly well suited for repetitive fast gas chromatography.

As used herein, "fast gas chromatography" means the analysis of a sample by gas chromatography in a shorter period than what previous gas chromatographic methods could separate the same compounds.

BRIEF DESCRIPTION OF THE DRAWINGS

FIGS. 4a-f are gas chromatograms for a gas sample containing various moieties having 1-6 carbon atoms.

DETAILED DESCRIPTION OF THE INVENTION

Figure 1:
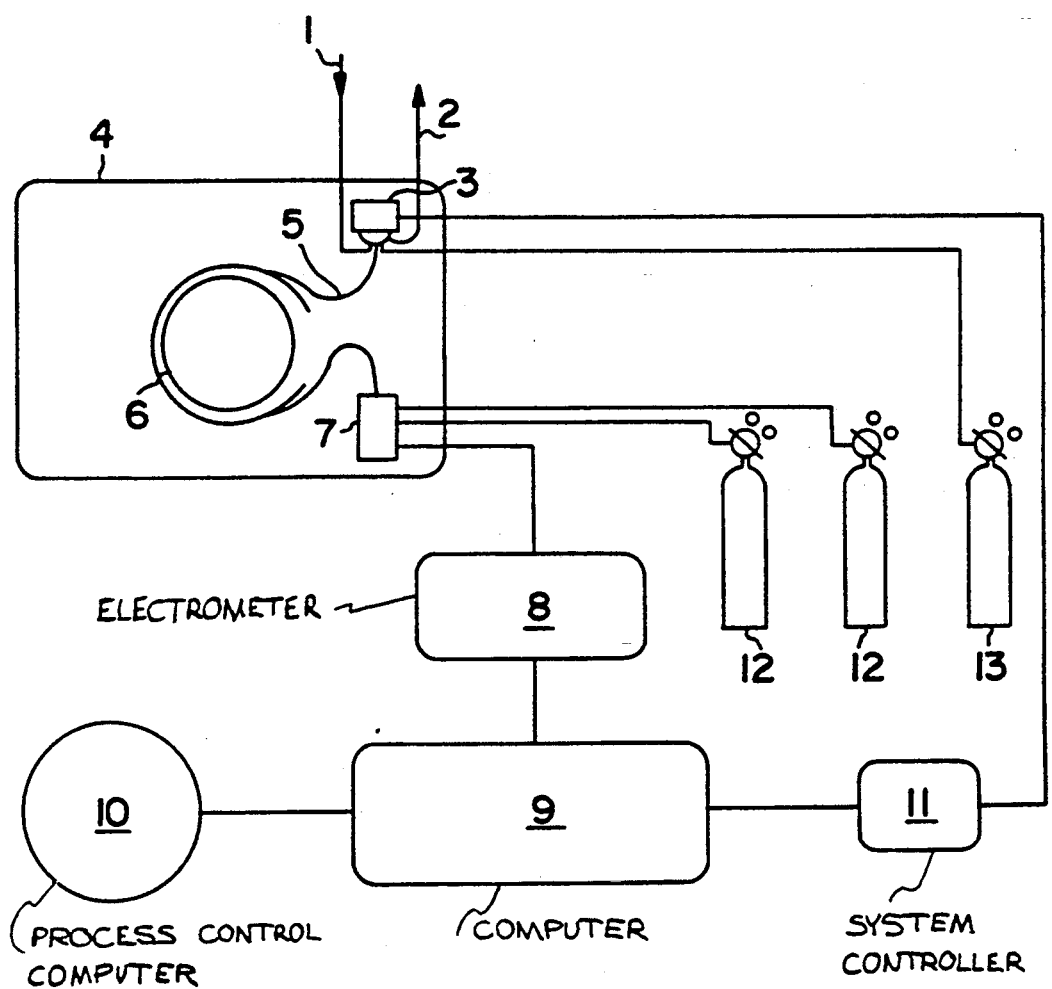
FIG. 1 is a schematic diagram of the fast gas chromatographic apparatus.

One embodiment of the method and apparatus of the present invention is depicted in FIG. 1. Referring to FIG. 1, the sample enters through conduit (1), flows through the sample injector valve (3), and exits through a vent (2). The sample is injected into the chromatographic column (5) which in a preferred embodiment is coiled around the fast temperature programming module (6). The sample flows through the chromatographic column and into the flame ionization detector (7). The injection valve, chromatographic column, fast temperature programming module and flame ionization detector are contained in a temperature controlled enclosure (4). Fuel gases, hydrogen and air (12), are supplied to the flame ionization detector and carder gas (13) is supplied to the injection valve from sources outside of the enclosure.

The flame ionization detector produces an electrical signal which is fed to an electrometer (8). The electrometer in turn produces another electrical signal which in turn is sent to the computer (9) which contains the various analog and digital input/output boards and suitable communications boards to interface with a process control computer (10) and a system controller containing an injector valve interface circuit (11). The process control computer receives the data regarding sample component concentrations and is programmed to manipulate process variables to maintain control of the process. A stream selector (not shown) can optionally be employed to select a particular sampling stream from multiple sources, if desired.

The method and apparatus for conducting fast gas chromatography consists of seven separate but interdependent systems: flow regulation, sample injection, partitioning column, temperature controlled oven, component detection, data acquisition and reduction, and system control. The differentiating factor between fast gas chromatography as described here and conventional gas chromatography is an emphasis on fast separation, rapid detector response along with fast data acquisition and integration of the data.

The flow regulation system provides a controlled flow of carder gas and other make-up gases as required by the system to perform a separation of components in a controlled and predictable manner. The flows may be constant or varied in a preprogrammed manner. Flows may be controlled by means of flow controllers or by controlling the pressure drop across the column or other flow restricting devices.

The preferred method of providing flow regulation is by using a conventional pressure regulator to control the column head pressure and venting the column at or near atmospheric pressure.

Sample injection is performed by a device capable of placing a portion of sample on the front end of the column, the sample having a plug flow profile, with sharply defined boundaries, the plug having a width of no more than 50 milliseconds; that is, the physical length of the sample plug placed on the column divided by the linear velocity of carder gas in the column shall be no more than 50 milliseconds, preferably less than 25 milliseconds and most preferably less than 10 milliseconds. This requires a fast operating injection device which contributes little or no mixing of the undiluted sample band with the carder gas.

A commercially available valve was found to be suitable for this application, the Valco Instruments Model VIII valve equipped with an internal sample loop and low dead volume fittings. The use of the internal sample loop provides sample widths suitable for operation in this apparatus. Sample bands injected with this kind of valve can have widths as small as 10 milliseconds or less. The performance of the Model VIII valve is surprising in that the valve is designed for sampling of liquids. It was first believed that this valve would not perform adequately and that it would broaden the sample width; however, this valve outperformed all other valves tested in this application. Other advantages of this particular valve is that it also provides very reproducible sample volumes during its use and is able to perform many operations without extensive maintenance.

The chromatographic column used for fast gas chromatography must be capable of quickly providing the separation of several components. Several methods of achieving this have been reported in the literature; most include the use of short, small bore capillary columns with higher than normal carder flow rates. The selection of column and operating conditions is very application dependent and those with skill in the art are able to select the appropriate column for a given application. Optionally, various column switching techniques, such as back-flushing and heart-cutting, may be used if care is taken to avoid dead volume in the flow path.

The chromatographic columns suitable for use in the invention are commercially available and preferably have a low mass so they can rapidly respond to heating or cooling changes. Illustrative of such columns are the fused quartz capillaries, fused silica capillaries, borosilicate capillaries, and the like, of which fused silica is preferred. The column may also have a stationary phase inside coating and an outer protective coating. Illustrative of said stationary phases are the following: CARBOWAX TM 20M; CARBOWAX TM Amine; Omegawax TM s 250 and 320; Petrocol TM s DH, DH 50.2, DH 150, 2887, EX2887, and 3710; PTE TM s-5 and -5QTM; SP TM s -2331 and -2560; SPB TM s-1, -1 sulfur, and -608; Sup-Herb TM ; VOCOL TM ; dimethyl siloxane, phenylmethyl siloxane, and the like, in series or alone with the choice of coating dependent on the type and complexity of the sample to be analyzed. Columns with such stationary phases are typically operable over a temperature range of subambient to more than 250° C. Such columns are available from Chrompack, Supelco, Inc., J&W Scientific Co., Restek, Hewlett-Packard, as well as other companies. In addition, conventional open-tubular columns have an inside diameter of about 0.05 mm to about 0.5 mm, but this invention is not limited by such a size range. Preferably, the diameter of the column should be as small as possible.

Typically, the chromatographic column is coiled around a column cage and placed in a temperature controlled oven. The number of coils required for the column depends on its total length, its diameter; the diameter, length, or other characteristic dimension of the heating device. Choice of said chromatographic column length is dependent on the boiling point range of the mixture to be separated and the desired component resolution. If necessary to accommodate the length of the column, the coils may overlap each other although this practice is not preferred. If desired, one or more columns containing different stationary phases can be used in series with each other. Such choices of stationary phase depend on the nature of the materials to be separated and are readily apparent to those with skill in the art. The chromatographic column is heated by conduction through an inert heat transfer fluid, typically helium, nitrogen and air, most preferably air or nitrogen, that has been contacted by the heater.

The length of the column is preferably as short as possible without sacrificing the resolution of the sample components. The purpose of the shorter column is to optimize the resolution level per time, not the best possible resolution of the samples. Preferably, low dead volume fittings are employed to connect the column to the sample injector and the detector.

For fast gas chromatography, the preferred column is a short section of a commercially available capillary column typically less than ten meters in length with an inside diameter of 0.32 millimeters or less. A carder gas having a linear velocity of greater than 200 centimeters/second and sometimes operating at velocities exceeding 300 centimeters/second is used. For example, a 10-meter long by 0.32 millimeter inside diameter Chrompack $Al_2O_3$/KCl column with a carder flow of 13 milliliters per minute and at a temperature of 80 degrees Celsius will give complete separation of methane, ethane, ethene, ethyne, propane and propene within 15 seconds.

A device or devices capable of controlling the temperatures of the chromatographic column, sample injector, and detector to within 2–3 degrees Celsius, or better, of a set point is required. Typically, the device is a temperature controlled enclosure similar in design to an oven. Such a device must be capable of controlling temperatures typical of conventional gas chromatography. In particular, all connections between the sample injector, chromatographic column, and detector, must be maintained at a temperature high enough to prevent hold-up of the sample as it flows from one system to the other.

The level of the various components contained in the sample are detected as they leave the chromatographic column by means of a suitable detector. This detector produces an electrical signal which is proportional to the concentration or amount of sample component leaving the column. The detector must be able to respond to changes in component level on the same time scale as the changes occur. For fast gas chromatography, this requires a time constant of no more than 5 milliseconds preferably about 2 milliseconds. These values are well outside the manufacturer's specified time constants. Typically, a manufacturer's time constant for a detector was on the order of between 100 milliseconds to 1 second. Very stringent requirements are placed not only on the detecting mechanism, but also on the path of the sample components from the injector to the detecting element. Excessive dead volume anywhere along the system will cause broadening of the component peak with a resulting loss of resolution.

The two detectors most commonly used in gas chromatography are the flame ionization detector and the thermal conductivity detector. Either type of detector has the potential to meet the requirements for fast gas chromatography; the selection of the type of detector employed is application dependent. Other types of detectors can also be used if they meet the time response requirements defined above.

The flame ionization detector has been demonstrated to meet the above requirements if the internal volume of the detector is designed or modified to minimize band broadening of the component peaks after entering the detector. The detecting mechanism within the flame ionization detector is inherently fast. For use in fast gas chromatography, the amplifier system used to amplify the extremely low current signal generated by the detector into a voltage signal must be equally fast. An amplifier of this type, or electrometer as they are commonly referred to in the art, must have a time constant of no more than 5 milliseconds, and preferably faster.

A flame ionization detector also employs fuel gases in order to operate. Typically, hydrogen and oxygen or air are the gases employed with hydrogen and air preferred in the operation of the fast gas chromatographic equipment.

A suitable thermal conductivity detector can also be made practical if its dimensions are such as to have a flow path compatible with the above mentioned requirements and the detecting elements are fast enough to reflect changes in stream composition in a timely fashion as mentioned above.

A preferred detector used in the fast gas chromatograph described herein uses a flame ionization detector sold as a part of a process gas chromatograph by Applied Automation, a division of Hartmann & Braun. It has been modified to reduce the dead volume in the flow paths to an acceptable level and to use a smaller flame tip.

Figure 3A:
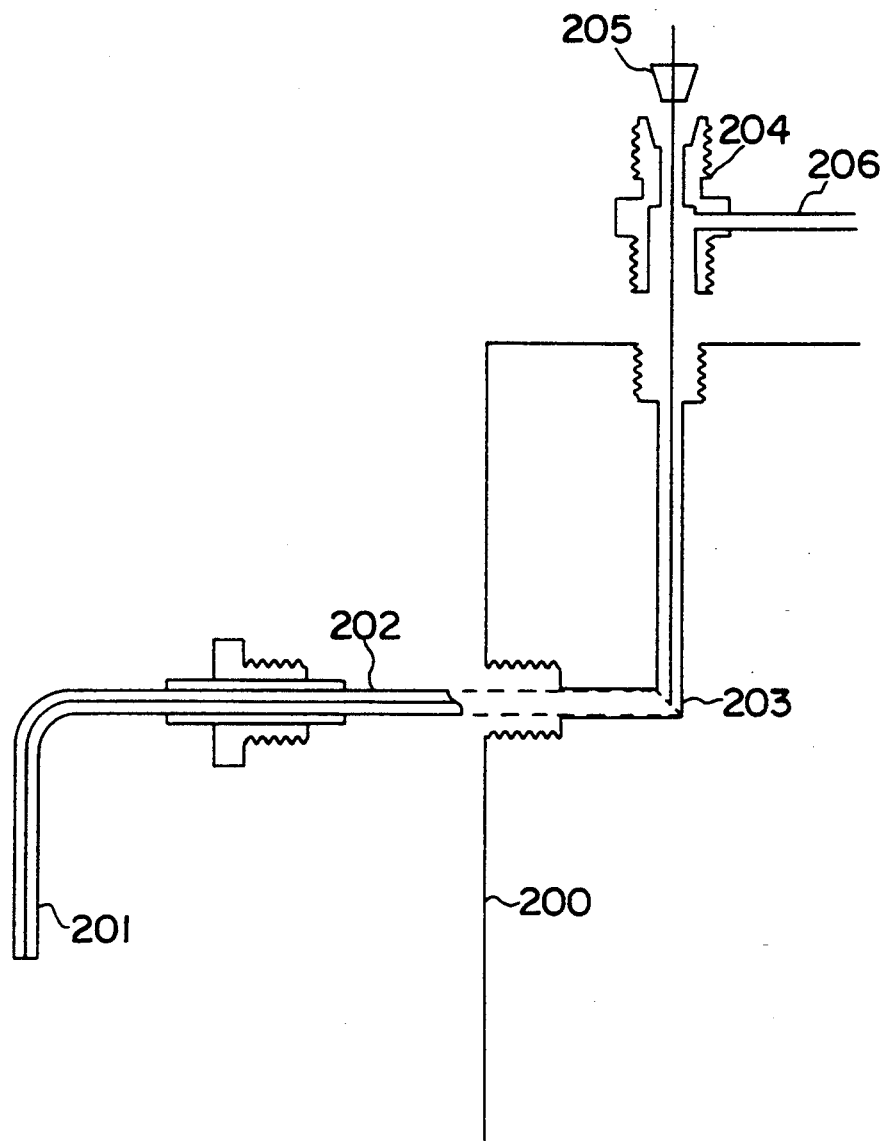
FIGS. 3a and 3b are schematic diagrams of the modifications made to the flame ionization detector and digital interface card which may be employed in the fast gas chromatograph.

As shown in FIG. 3a the 1/16" outside diameter (OD)×0.035" inside diameter (ID) (0.158 cm OD×0.090 cm ID) flame jet tube 201 in the detector 200 was replaced with a 1/16" outside diameter×0.020" ID (0.158 cm OD×0.0508 cm ID) stainless steel tube. In addition, a 1/16" (0.158 cm) OD×0.020" ID (0.0508 cm) Teflon® tube was inserted into the 1/16" (0.158 cm) conduit running to the flame jet 202. The inlet of the flame jet was cut at a 45° angle to prevent flow blockage at the 90° bend in the conduit 203. Finally, the column connector was replaced with a stainless steel male fitting 1/16" (0.158 cm) tube to 1/16" (0.158 cm) normal pipe thread (NPT) 204. A hole was drilled into the side of fitting and a piece of 1/16" OD×0.035" ID (0.158 cm OD×0.090 cm ID) stainless steel tubing 206 was silver soldered to the connector for flame gas fuel supply to the detector. A graphite ferrule 205 was employed to seal the chromatographic column to the flame ionization detector. As noted previously these modifications were made to reduce the amount of dead volume in the detector.

The electrometer supplied with this chromatograph was also used with modifications to enhance the response time to 2 milliseconds. The low and high gain resistors (R32 and R31) were changed to 50M ohm and 500M ohm values. Capacitor C48 was removed and capacitor C49 was changed to 20 picofarads. The gain switching circuit of the electrometer was isolated by cutting a trace on the detector board, and an external digital signal was connected to the circuit.

The electrometer was intentionally modified to allow some noise to pass through to the data acquisition system. Many of the peaks produced by the apparatus were in the same frequency range as the electrical supply noise, i.e., 60 Hertz. Therefore, the fast GC was designed to allow most of the noise to pass through to the digitizer so as not to filter out the signal peaks obtained from the detector. The software used to operate the system contained one of several data smoothing techniques to reduce the level of noise in the reported data.

The data acquisition system must be able to collect data at a rate that accurately describes a sample component as it leaves the column and is detected. In the case of a sample and hold analog to digital acquisition system as is commonly used, typically 20 to 30 points, and preferably more, are required to define a component or, just as importantly, the space between components. Because the time width of components can approach the width of the sample plug entering the column, it is feasible to have component widths of less than 10 milliseconds. The data acquisition system must then be able to digitize and store the detector signal at a rate of at least 100 points per second typically greater than 500 points per second and preferably at a rate exceeding 1000 points per second. The raw data thus obtained must then be reduced to analysis values, sometimes referred to herein as integration, which describes the number and amount of the components within the sample.

Gas chromatographs typically digitize and store data at rates of less than 100 points per second, usually at a rate of 20–30 points per second. The higher number of points per second achieved by fast gas chromatography was realized by the modification of the electrometer and the data collection and integration program described herein. A computer board installed in a personal computer was necessary to collect the digitized results and process the increased rate of information collected. Preferably, the board has a wide dynamic range (16 bits) and is commercially available. The application of a computer board of this speed to process and collect the data is novel for gas chromatography applications.

In the case of a process gas chromatograph, there are two times which are important to consider, the analysis time and the cycle time. The analysis time is the time required for all of the sample components to be separated, to leave the column, and to be detected and the resulting signal acquired. The cycle time is the amount of time required between sample injections and includes the analysis time, any additional time for the column and detector systems to reset back to initial conditions, and any data reduction time. In the ideal system, the cycle time and the analysis time are equal, that is, no additional time is required for clean up or data reduction, a situation frequently achieved in conventional process gas chromatography and highly desirable in process fast gas chromatography.

There are several approaches to achieving this minimum-cycle-time system. One approach, often taken in conventional process gas chromatography, is the reduction of component data to composition values as the sample component data is acquired. At the end of the analysis time, the data has already been reduced and presented to the user, and a new cycle can begin immediately. Contrary to the teaching of the prior art, the present invention employs an alternative approach that permits the use of one of the many excellent chromatographic data reduction software packages available on the open market, including but not limited to Chromperfect by Justice Innovations, Inc. By using a high speed computer, the data acquisition and instrument control are performed as an interrupt driven background task while the data reduction of previously acquired data is done as a foreground task. This results in a delay of about 10 seconds in presenting analysis results, depending on the amount of data to be reduced and the speed of the computer, but it permits very high data acquisition rates and enhanced post-processing capability without sacrificing cycle time.

More specifically, traditional software programs for gas chromatography have been operated sequentially one step after another. The sample injection step is followed by a period wherein the electrical signal generated from the detector is acquired and the gas chromatograph is controlled by the software. After all the information has been acquired from the detector, the data is processed, known as integration, and the data is finally reported. In traditional gas chromatographic software, each step essentially waits for the completion of the previous step to be completed before the next step is initiated and all of the steps must be completed before the next cycle is initiated.

The software of the fast gas chromatograph of the invention is made up of two concurrently operating systems. The first system handles data acquisition and control of the apparatus while the second system processes and reports the data. By operating concurrently, more information can be processed in a given period of time which allows the equipment to be operated at higher speeds.

The fast gas chromatography software also processes the information differently than traditional gas chromatography software packages. Typically gas chromatography software programs only integrate the data. The fast GC software first smoothes the data, then integrates the data and also provides feedback to the process computer. As mentioned above, because the fast gas chromatography digitized output has not been filtered, since filtering would remove much of the noise, data smoothing techniques have been incorporated in the software. These techniques are well known in the art, in particular, a Savitzky-Golay data smoothing technique was used in the present invention, Savitzky, A. and Golay, M. J. E., "Smoothing and Differentiation of Data by Simplified Least Squares Procedures," *Analytical Chemistry*, 36, 1627 (1964).

Preferably, the fast GC software also makes use of a communication board with an on-board microprocessor to report the data to a process control computer. The purpose of the communication board is to link the personal computer which operates the gas chromatographic apparatus with the process control computer. The addition of the communications board allows the process control computer to access the data without interrupting the personal computer operating the gas chromatograph. The addition of the communications board was necessary to transfer the information generated by the fast gas chromatograph to the process control computer without causing system delays.

A process gas chromatograph is designed to run automatically, that is, completely unattended. In order for it to do that, a system controller must be included as part of the system. This controller controls various peripherals such as sample injection valves, amplifier gains, and signal zero levels during the course of an analysis ran. It is also responsible for selecting streams if the chromatograph is set up as a multi-stream analysis system. Most events are performed at preset times in the analysis cycle. The resolution of the time base used must be commensurate with the times at which sample components move through the column. In the fast gas chromatograph, a time base with a resolution of at most 10 milliseconds is used. This is compatible with gas sample components which come out of the column only tens of milliseconds apart.

In order for the various components of the system to perform properly within the system, interface cards are sometimes required for computer control of solenoid valves, amplifier gain and stream selection. In conjunction with the interface cards, software is also employed to sequence the equipment, and to operate and control the valves in the field. This software is frequently written to a particular standard and is dependent upon many factors, including the computer equipment and software used, the valves and controllers which are installed and any company standards which are employed. In the present invention, Union Carbide Control Software was used to control the operation of remote process equipment.

Figure 2:
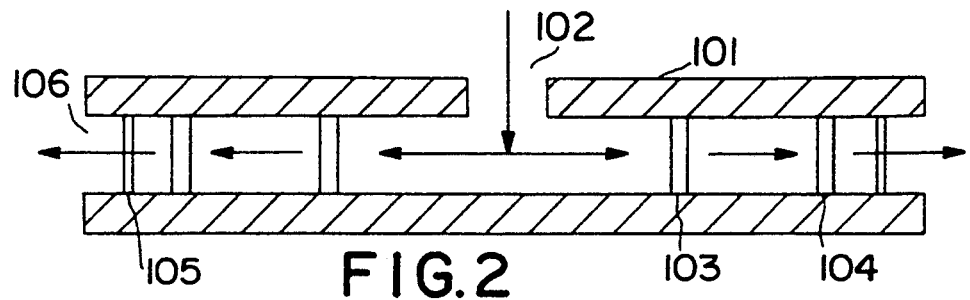
FIG. 2 is a schematic diagram of the temperature programming module which may be employed in the fast gas chromatograph.
Figure 2A:
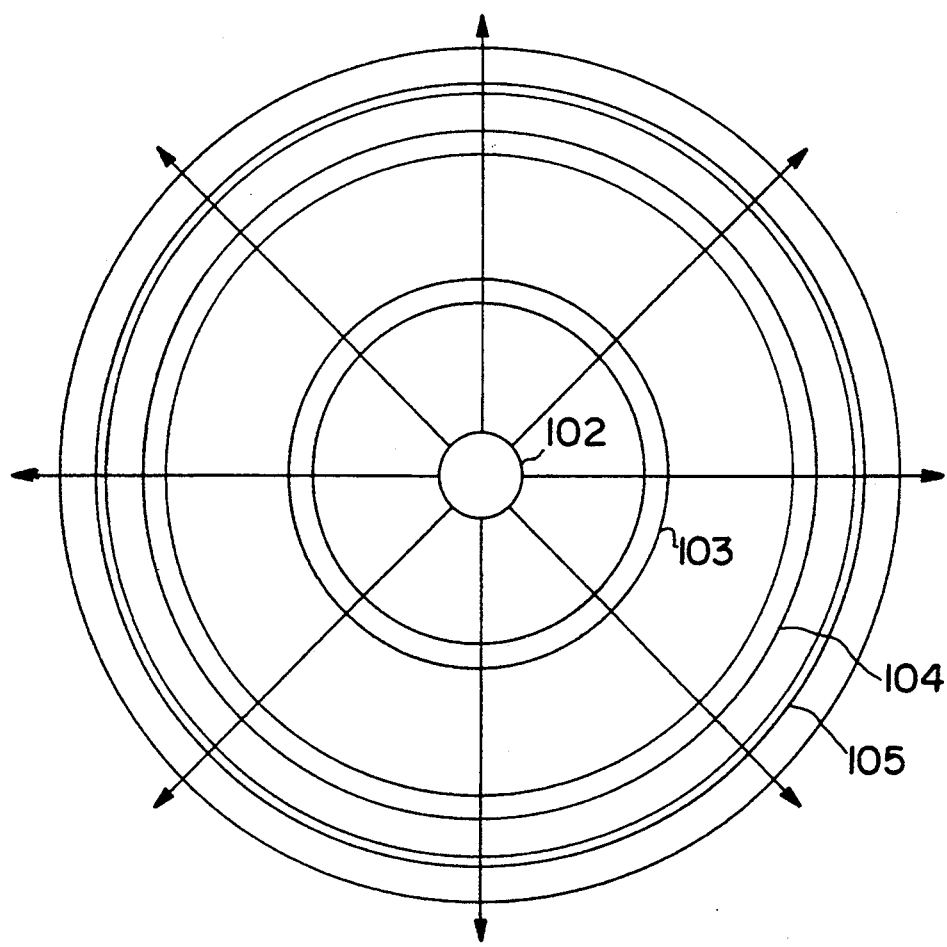
FIG. 2A is a top view of the temperature programming module which may be employed in the fast gas chromatograph.

In an especially preferred embodiment of the present invention, a heating device, referred to herein as a fast temperature programming module, is employed which can rapidly heat the chromatographic column while also being capable of rapidly cooling the column when required. The chromatographic column is cooled by passing unheated heat transfer fluid over the capillary column, preferably perpendicular to the flow of the sample and carrier gases within the capillary column. The temperature program module as depicted in FIG. 2 comprises an optional insulated body (101) in which there is an inlet means (102) for a gas or fluid that acts as a heat transfer fluid with said fluid passing first through an optional baffle (103) then over a heating means (104) followed by passage of the heated medium over and around the gas chromatographic column(s) (105) which is preferably held in place with brackets (not shown) and then exiting through an exit means (106) into the gas chromatograph housing enclosure or the atmosphere. The fast temperature programming module is suitable for conducting programmed-temperature, rapid gas chromatographic analyses of compounds whose boiling points differ by as much as 250° C. in times of less than about two minutes, preferably less than about one minute. The heating device can be fabricated in various shapes illustrative of which are circular, cylindrical, rectangular, torodial, spherical, linear and the like, preferably in a modified-circular shape as illustrated in FIG. 2.

The body of the heating device is fabricated from a machinable material capable of withstanding the high temperatures and other hostile environments that might be encountered in a laboratory or manufacturing locale, illustrative of which materials are the ferrous metallic compounds such as steels; stainless steels such as stainless steel 304 and stainless steel 320; cast alloys, steels lined with alloys, cast iron, and wrought iron; nonferrous metallics such as aluminum, copper, silver, gold, molybdenum and molybdenum alloys, nickel and nickel alloy, tantalum and tantalum alloys, titanium and titanium alloys, gold or silver plated steel, copper, iron, and the like; nonmetallic materials such as composite material illustrative of which are carbon-fiber composites, graphite-fiber composites, fiberglass composites, Marnite P (Johns-Manville Corp.) and the like, glass, tempered glass, ceramics such as fused silica, chemical porcelain, Zircar 100 (Zircar Products, Inc.), stoneware, refractories, Aremcolox TM 502 series of machinable ceramics (Aremco Products, Inc., Ossining, N.Y.) such as the glass ceramics, 502-400 and 502-600, the aluminosilicate ceramics 502-1100 and 502-1200, the silica-foam ceramic 502-1250, and the high alumina ceramic 502-1400; sintane, plastics such as polyimide, rigid polyurethane foam, phenolics, melamines; and the like. Particularly useful body construction materials are stainless steel 304 and ceramics.

The sides of the heat transfer fluid inlet to the heating device can have a variety of shapes to facilitate the flow of heat transfer fluid which is usually a gas including perpendicular to the diameter of the heating device, at an angle to the diameter of the heating device, curved toward the outlet, and the like. After passing through the inlet, the inert gas passes through an optional baffle that ensures there will be an essentially uniform flow of inert gas without dead spots through the chamber to the heater. The baffle can be of various cross-sectional shapes illustrative of which are square openings, circular openings, oval openings, hexagonal openings, and the like. The baffle can be constructed of various materials illustrative of which are those enumerated above for body and heater construction. A particularly useful baffle material is stainless steel 304. Pressure and/or flow of the heat transfer fluid is controlled by time, temperature, and pressure programmer, illustrative of which are needle valves with a pressure regulator. Heat transfer fluid is used to control the temperature program of the column and its contents. Variables include the flow rate and the inlet temperature of the heat transfer fluid. Profiles of the temperature program are controlled by varying the energy, typically the voltage or current, to the heater screen.

The heating means can be any source of energy to the heat transfer fluid, preferably the heating means is an electrical resistance or induction heater that is electrically insulated from the body of the heating device The heating means is constructed in a variety of ways including from a single or multistrand wires or ribbons that are sheathed or unsheathed and arranged in a helical pattern, in a mesh or screen pattern, in a grid pattern illustrative of which is a square, diamond, triangular, round, oval, and the like pattern with said wires capable of being electrically heated to high temperatures in short periods of time. The heating means is positioned from about 30° to about 150° relative to the longitudinal axis of the conduit. Preferably the heating means is substantially perpendicular to the conduit. It is preferred that the heating means have a low mass so it can be rapidly heated and cooled. The elements are typically wires made of metallic, electrical conducting substances that will quickly and reproducibly heat and maintain high temperatures without rapidly degrading or otherwise deteriorating when electrical current is applied. Such resistance materials are often alloys and have small temperature coefficient of resistance. Illustrative of such substances are steel, stainless steel, stainless steel 304, copper, aluminum, bronze, and the like. Sheathing materials include steel, ceramic, porcelain, glass, quartz, and the like. The heating means is preferably electrically activated and controlled by a computer controlled voltage supply.

The chromatographic column inlet is connected to a supply of carder gas and an injection means for introduction of sample into the column. Suitable carder gases include but are not limited to hydrogen, nitrogen and air. Those skilled in the art of gas chromatography are cognizant of the design of such supply/inlet ports for gas chromatographs. However, it is important that the sample injection system be capable of delivering quantities from about 0.05 to about 15 microliters or more, preferably from about 0.10 to about 2 microliters, and most preferably about 0.25 to about 1.0 microliter of sample to the chromatographic column. The outlet from the chromatographic column in the heating device is connected to a detection device that directly or indirectly monitors a physical or chemical property of the effluent gas containing the separated components. An illustration of such devices was included above.

The assembly of inlet system, heating device, chromatographic column, exit port, and detector are usually contained in a protective enclosure that is maintained at a constant temperature. The protective case may be constructed of various materials illustrative of which are metals, plastics, composites, and the like.

The heater is able to modify the temperature of the column and its contents very rapidly, thereby enabling fast temperature programmed gas chromatography to be performed. The heating means is capable of providing temperature within the column from subambient temperatures, i.e., such as 0° C. if a refrigerated heat transfer gas is employed, to about 300° C. The low mass and high surface area of the heater screen enables efficient heat transfer and rapid heating and cooling of the heating screen. The rapid heating and cooling is imperative in fast gas chromatography because the heating and cooling cycles should match the speed of the chromatographic separation. The invention provides heating rates of at least 1° C. per second, typically at about 5° C. and most preferably at about 10° C. per second over the temperature range. The temperature cycles produced by the fast temperature programming module must be reproducible in order for temperature programmed fast gas chromatography to give reproducible component retention times and accurate results.

The following listing of Equipment in Table 1 illustrates apparatus that may be used to construct the fast gas chromatography apparatus as depicted in FIG. 1.

TABLE 1

Figure 3B:
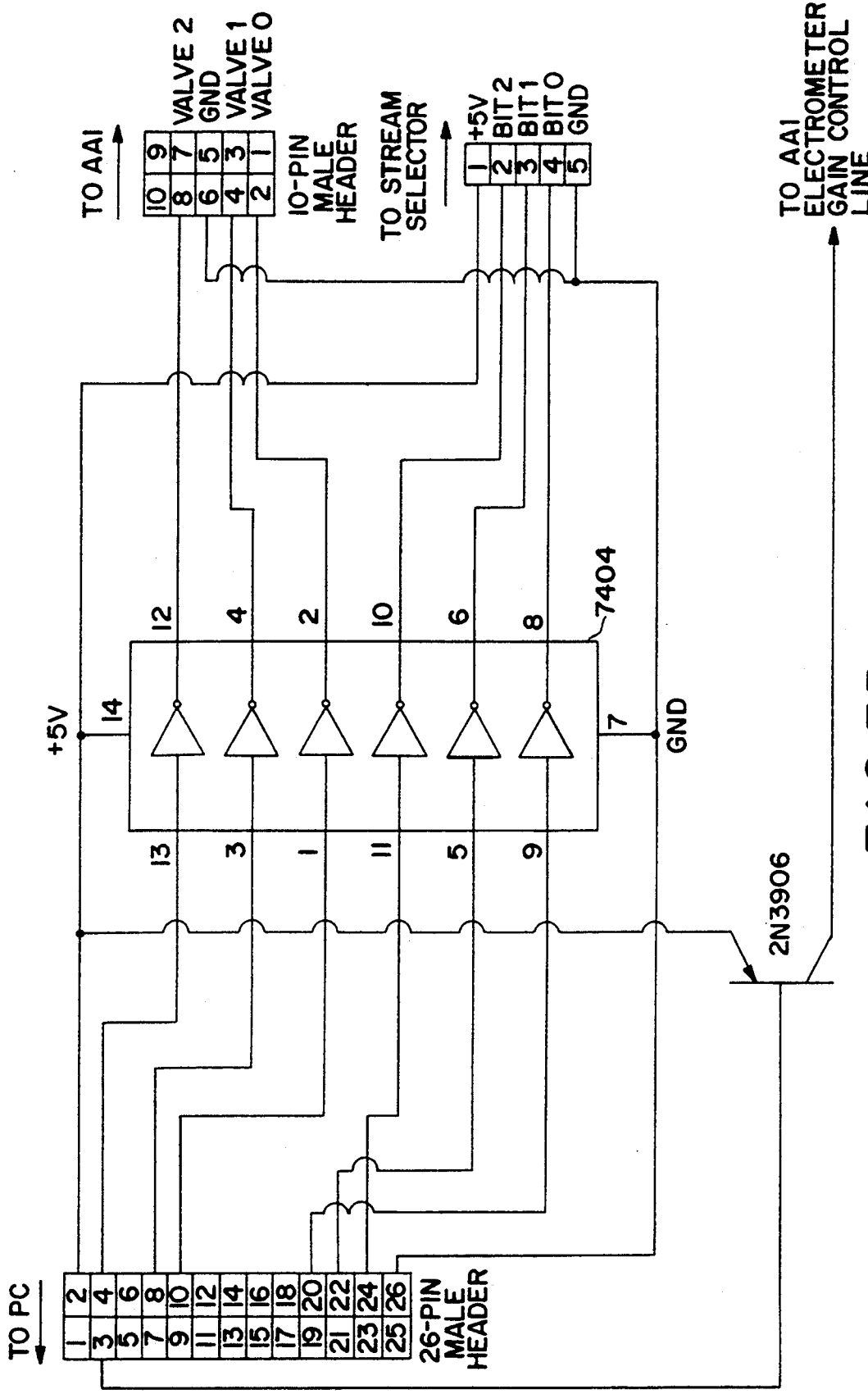

| | |
|---|---|
| Injector Valve | Valco Model III Part AN-600 (0.5 microliters) |
| Personal Computer | ZEOS 33 MHz 80486 with 4 megabytes of memory and 130 megabyte hard drive. |
| Analog to Digital | Keithley/Metrabyte DAS-HRES 16 bit Adapter |
| Digital Adapter | Keithley/Metrabyte PIO-24 digital I/O board |
| Server Communication | Industrial Computer Source ACL-8-IIR+ with connector |
| Software | ChromPerfect, Union Carbide Control Software and AAI Application Personal Computer Software |
| Chromatograph | Applied Automation Inc. with flame ionization detector |
| Stream Selector | Union Carbide Type 43 |
| Detector | Flame Ionization Detector available from Applied Automation modified as described herein. |
| Digital Input/Output Interface Card | As depicted in FIG. 3b, constructed exclusively for this application. |
| Chromatographic Column | 10 m × 0.32 mm I.D. $Al_2O_3$/KCl fused silica capillary PLOT column with a 5 micrometer stationary phase thickness (Chrompack Part #7515) |
| Temperature-controlled enclosure | Applied Automation, a division of Hartmann & Braun |

The Chromperfect software package was also modified by the supplier Justice Innovations to enable the fast GC apparatus to operate. The software package as originally provided was not able to integrate the data quickly enough to keep pace with the amount of information being generated by the detector. Consequently, Justice Innovations modified the program to eliminate the delays thereby overcoming the original data integration limitations for conducting fast GC.

The fast gas chromatographic technology is readily employed to rapidly determine the compositions of process streams and these compositions can be used for process control. As used herein, process variables are defined as any variable in the system that are uncontrolled variables (such as uncontrolled flows, compositions, temperatures in the process that are used by personnel for monitoring the operation of the process equipment), manipulated variables are defined as the variable in the process that is directly manipulated to produce a process control (such as a valve position or a set point on a control loop), and control variables are the variables that the manipulated variables are trying to control at a specific value (such as a composition, temperature, or pressure at a location, a flow rate, reflux ratio or the like). As used here, process control is defined as the handling of the manipulated variables such that some other control variables are maintained at or near a set point. The appropriate manipulated and control variables are both process and apparatus specific. For example, a person skilled in the art would know how to design a control systems for a distillation column in which set points for reflux ratio, feed rate, bottoms flow, reboiler duty, and the like are manipulated to control distillate compositions. Similarly a person skilled in the art would know how to design a control system for a polyolefins polymerization reactor in which gas composition is manipulated to control polymer properties.

Applications for fast GC include but are not limited to analysis of feed streams, streams removed from a single unit operation (for example a distillation tray or the middle of a plug flow reactor), internal process streams, recycle streams, blow off gases, vent gases, purge gases, catalyst concentrations in various streams and the like. The concentrations of the various components in the stream would then be used in controlling the process. Fast gas chromatography can be used to enhance the precision of control of these processes, reducing process variability and improving product quality and the like. Fast gas chromatography can also be used to control non-steady-state processes, especially where concentrations can change rapidly. Fast gas chromatography can also be used to obtain the data needed for the development and verification of dynamic process simulation models.

Fast gas chromatography would be useful in processes where the reaction is very fast, such as an olefins furnace, where the reaction system can be accurately modeled, such a polymerization reactors, or in processes where accurate quickly obtained results would provide a composition profile, such as in a tubular reactor or multi-stage separation column. Those with skill in the art can readily apply the present invention to control process equipment or processes such as but not limited to, continuous stirred tank reactors, batch reactors, fluidized and backed bed processes, separation processes (such as distillation columns, scrubbers, extraction systems, refrigeration units, adsorption and absorption units, and pressure swing adsorption units), liquid or gas phase mixers, liquid/solid separation, catalytic reforming of hydrocarbons, dehydrogenation processes, catalyst testing, tail gas finishing, adsorptive heat recovery, and the like.

Fast gas chromatography can be employed in any process in which gas chromatography is currently employed. Fast gas chromatography is suitable for many processes including those that manufacture polymers, alcohols, gasoline and other hydrocarbon products, paints, industrial chemicals and the like. Among the many benefits derived from the use of the present invention include higher raw material efficiencies, reduced off specification production, improved purity products, reduced energy consumption, and reduced emissions during manufacture of the various products.

The Examples which follow are presented for the purpose of illustrating the invention and are not to be construed as unduly limiting the invention described by the claims. All pans and percentages are by mole % unless otherwise specified.

EXAMPLE 1

A fast temperature programming module, as depicted in FIG. 2, was constructed with a ceramic body and a heater screen that was connected to a Lambda Model LLS9018 programmable power supply. The heater screen was constructed of stainless steel 304 wire mesh having a wire diameter of 0.008 inches and a 50-mesh size. An air diffuser baffle was also constructed of stainless steel 304 wire mesh having a 700-mesh size. A 10 meter length by 0.32 mm inside diameter Alumina/KCl fused silica open tubular chromatographic column with a 5 $\mu$m stationary phase thickness (available from Chrompack) was place around the module. Flow of the heat transfer fluid (air, in this case) through the diffuser baffle and the heater screen was controlled by a regulator and needle valve that operated at up to 15 standard cubic feet per minute. The inlet or upstream end of the chromatographic column was connected to a Model VIII 0.5 $\mu$L internal volume diaphragm valve with zero dead volume fittings (Valco Instruments Co.) which was used to inject a gaseous sample into the column and provided a means for introducing the sample carder gas. The outlet or downstream end of the chromatographic column was connected to a flame ionization detector. All of these components which were placed in an insulated stainless steel-lined, temperature controlled, air-purged metal enclosure to protect it from hostile environments that might be encountered in a laboratory, a manufacturing plant, or other surroundings in which it might be used and to maintain an approximately constant, elevated temperature.

EXAMPLE 2

Hydrocarbon mixtures containing methane, ethane, ethylene, propane, propylene, 1-butene, cis-2-butene, isobutene trans-2-butene, isopentane, n-hexane, trans-2-hexene, 2-ethyl-1-butene, 1-hexene and trans-2-hexene were analyzed using various gas chromatographic techniques.

The retention times (RT) for separating the components and measuring the levels of the various components is presented in Table 2.

TABLE 2

| Peak | Isothermal 5-Meter RT (sec) | Temp Prog 5-Meter RT (sec) | Isothermal 10-Meter RT (sec) | Temp Prog 10-Meter RT (sec) | Process GC RT (sec) | Conventional Capillary GC RT (sec) |
| --- | --- | --- | --- | --- | --- | --- |
| Methane | 1.79 | 2.31 | 6.02 | 6.94 | — | 128 |
| Ethane | 1.87(1) | 2.43 | 6.69 | 7.44 | 509 | 144 |
| Ethylene | 1.92(1) | 2.8 | 7.08 | 7.75 | 557 | 163 |
| Propane | 2.14 | 3.44 | 8.24 | 8.82 | — | 208 |
| Propylene | 2.43 | 4.55 | 11.9 | 10.5 | — | 282 |
| 1-Butene | 3.92(1,2) | 10.8(1) | 27 | 16.4 | 197 | 416 |
| cis-2-Butene | 3.92(1,2) | 11.1(1) | 28.8 | 16.9 | 266(2) | 420 |
| Isobutene | 4.16(1) | 12.1 | 31.6 | 17.7 | 266(2) | 434 |
| trans-2-Butene | 4.46 | 13.2 | 35.7 | 18.6 | 266(2) | 446 |
| Isopentane | 5.29 | 15 | 43.1 | 21 | 367 | 476 |
| n-Hexane | 14.7 | 24 | 219 | 35.6 | 811(2) | 617 |
| trans-2-Hexene | 22 | 27.0(1) | >240 | 42.1 | 811(2) | 659 |
| 2-Ethyl-1-Butene | 23.3 | 27.5(1) | >240 | 44.3 | 811(2) | 668 |
| 1-Hexene | 25.3 | 28.3(1) | >240 | 45.6 | 700 | 677 |
| trans-2-Hexene | 27.7 | 29.0(1) | >240 | 47.7 | 811(2) | 688 |

(1) Partially Resolved
(2) Coelutes

The Process GC was a commercially available analyzer employing a typical column switching arrangement involving six different columns and 5 valves. The Conventional Capillary GC was a 50 meter by 0.32 mm inside diameter $Al_2O_3$/KCl column which was operated at 25 pounds per square inch head pressure. The temperature of the column was held at 50° C. for two minutes and the temperature of the column was ramped to 200° C. at a rate of 20° C./minute. When the temperature reached 200° C. the column temperature was held for two minutes.

As is readily apparent from the above example, the retention times using the Process GC and the Conventional Capillary GC were much longer than the fast GC methods shown in columns 1-4 of Table 2.

Figure 4B:
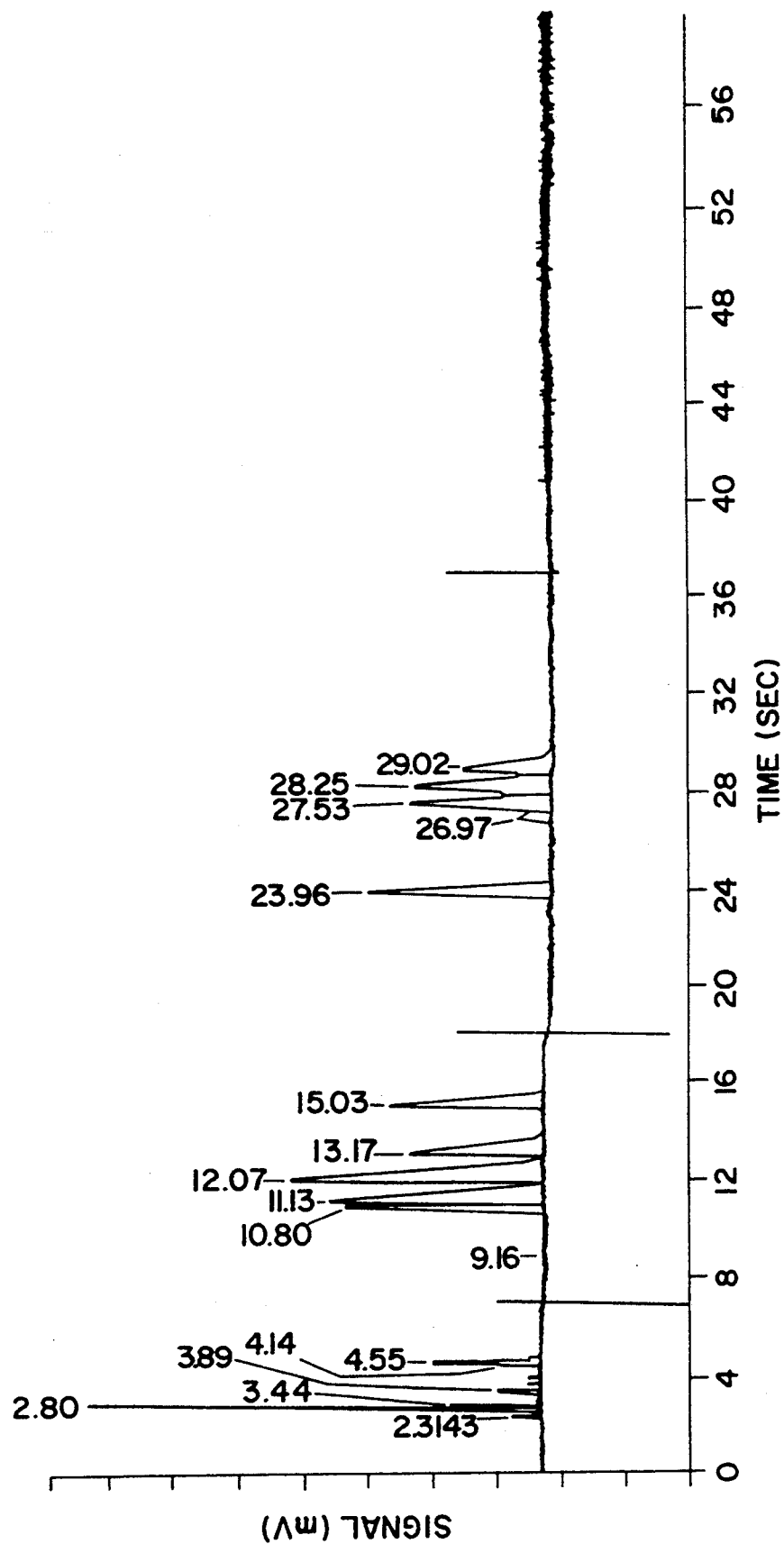

In employing the isothermal 5 meter column fast GC method, the column temperature of 110° C. was selected so as to separate the C6 fraction (1-hexene, trans-2-hexene, etc.) in the column in less than 30 seconds. While this goal was accomplished, the resolution of all of the early eluting components was not completed. FIG. 4a depicts the separation achieved in the 5 meter column.

With temperature programming a lower initial temperature (of about 80° C.) was employed and held for approximately 8 seconds, to achieve good resolution of the early eluting components. The temperature was ramped to 200° C. over 12 seconds and held for about 35 seconds to elute the C6 fraction. Because the resolution of all the components were not complete, see FIG. 4b, a 10 meter column was then employed.

Figure 4C:
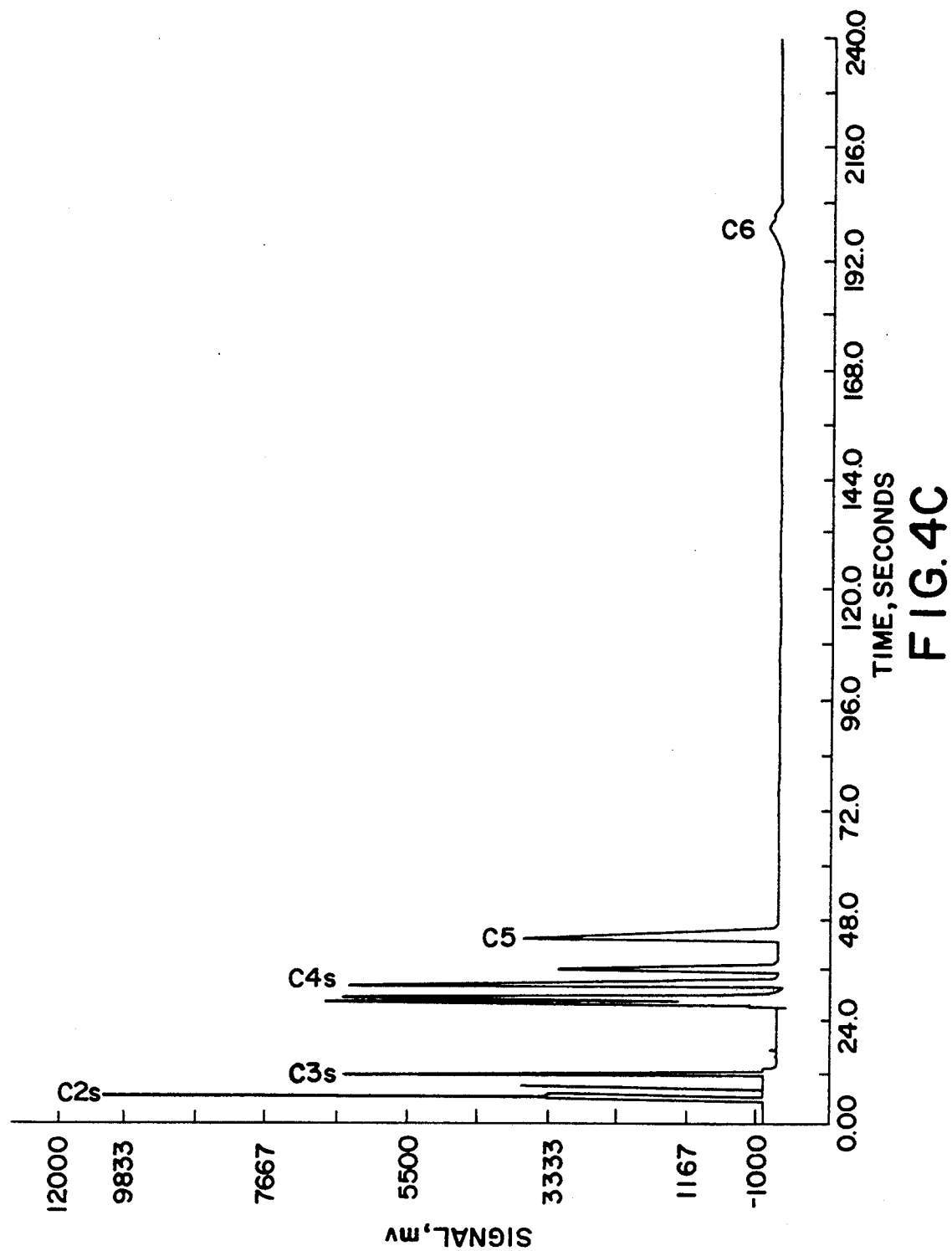

The 10 meter column was isothermally operated at about 110° C. As was expected, the retention times for the compounds were much longer than the isothermal 5 meter retention times. The resolution of the lower molecular weight compounds was improved, but some of the higher molecular weight fractions did not elute in less than four minutes, see FIGS. 4c.

Figure 4D:
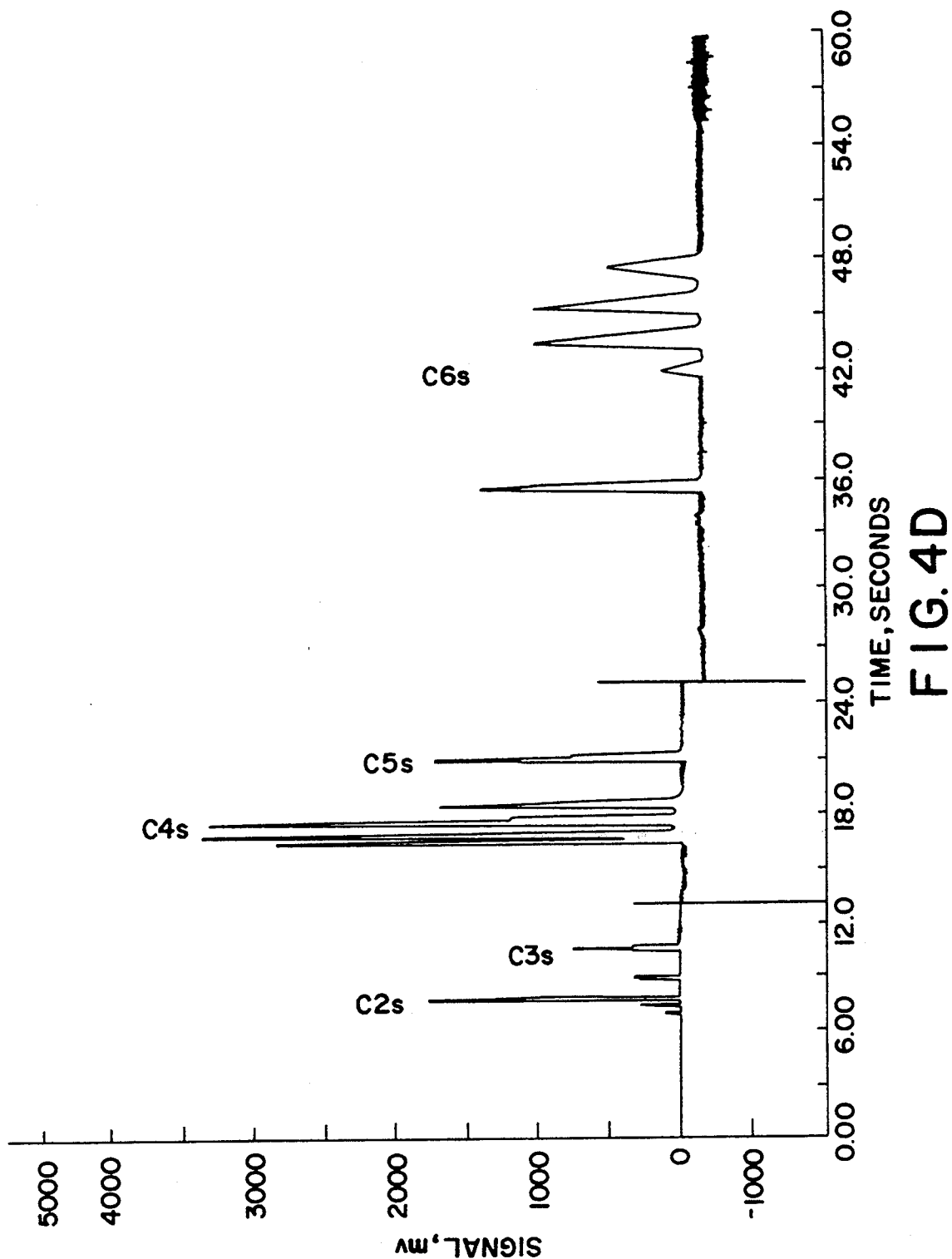

The temperature programmed 10 meter column was operated over a temperature range from about 90° C., which was held for about 10 seconds, to about 180° C. over a period of about 15 seconds and held at about 180° C. for about 50 seconds. All of the compounds were well resolved and the total analysis time was less than 1 minute, see FIG. 4d. This is a significant reduction in time to conduct the analysis when compared to the Process GC and conventional capillary GC, see FIGS. 4e and 4f respectively.

EXAMPLE 3

Fast gas chromatography was employed to rapidly determine the composition profile, i.e., the concentration of components at various locations (heights or trays) within a distillation column which separates ethane from ethylene). The fast GC was employed to measure methane, ethane, ethylene, acetylene, propane, and propylene concentrations in the reflux stream as well as several points located along the distillation column.

A fast GC, described in this invention and outlined earlier in Table 1, was used to perform this measurement. The analysis was conducted in isothermal mode. Instrumental parameters were was follows:

Instrument: Applied Automation Inc. (AAI) Optichrom Advance process gas chromatograph which is equipped with a Valco Model VIII 0.5 μL internal volume injection valve with low dead volume fittings and a flame ionization detector modified for high speed use. Data acquisition and processing is accomplished with a Zeos 33 MHz 80486 computer equipped with 4 Megabytes of memory and a 130 Megabyte hard drive with Super-VGA display.

Columns: 10 m×0.32 mm I.D. $Al_2O_3$/KCl fused-silica capillary PLOT column with a 5 μm stationary phase thickness (Chrompack Part #7515 (50 m in length))

Column Temperature: 80° C.

Injection System: Valco Model VIII 0.5 μL internal volume injection valve equipped with low dead volume fittings (Valco Part #AN-600E or #AN-700E).

Sample Volume: 0.5 μL

Detector: Flame Ionization that has been modified for high speed/capillary column analysis by minimizing dead volume and incorporating high speed signal amplification.

Carrier Gas: Hydrogen at a flow rate of approximately 13 mL/min (column head pressure is approximately 8 psig)

Detector Gases: Hydrogen at 35 mL/min Air at 650 mL/min

Cycle Time: 30 seconds

Figure 5:
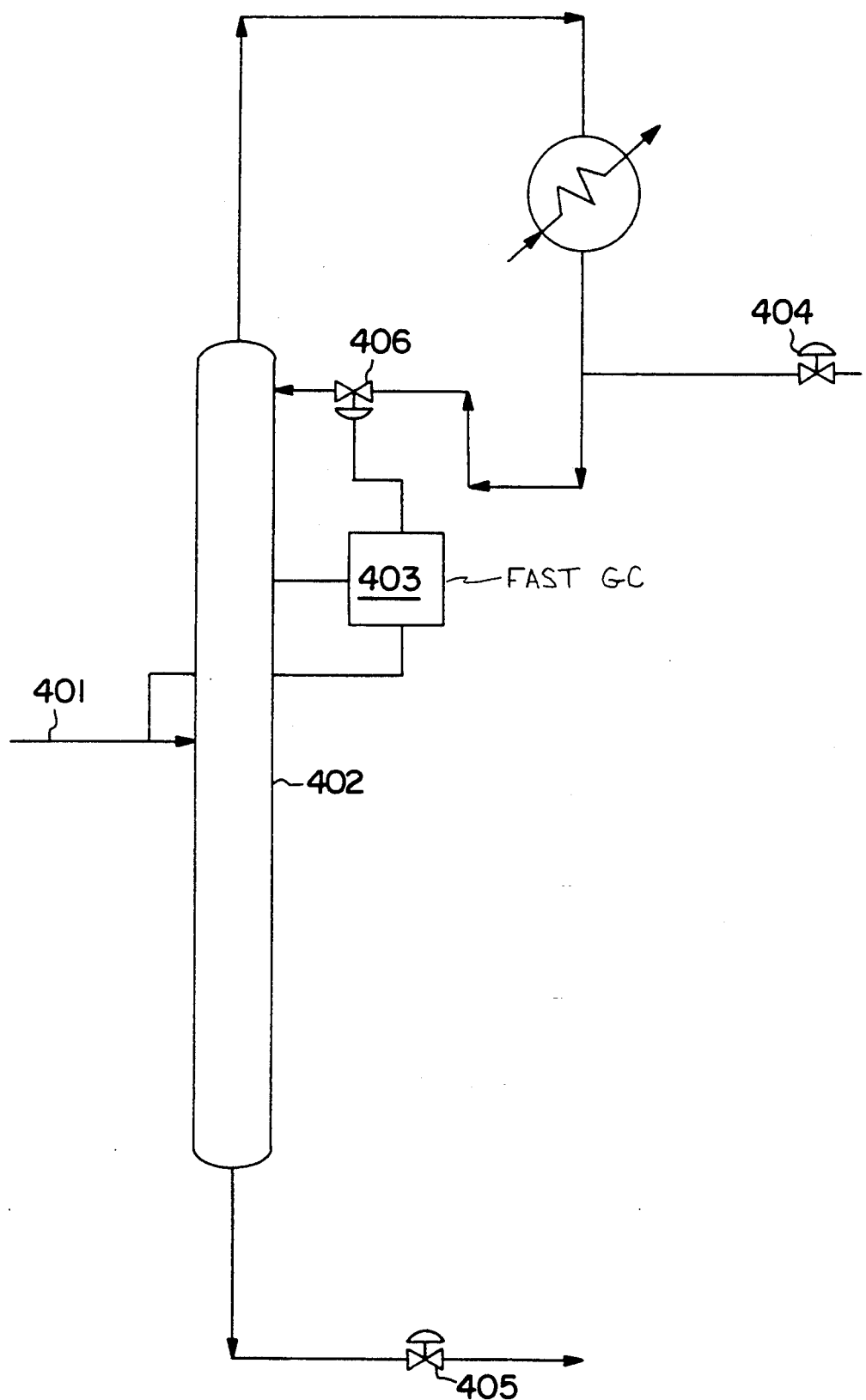
FIG. 5 is a diagram of a distillation column employing fast gas chromatography in the process control scheme.

FIG. 5 demonstrates the control scheme employed with fast gas chromatography. Sample taps were installed on the distillation column to provide a continuous, representative sample to the fast gas chromatograph. The fast gas chromatograph provides analytical results of the contents of the column. The analysis of the compositions at the selected sample locations is sufficiently rapid to detect the effect of disturbances to product withdrawal locations. The process dynamics are such that more frequent compositional analyses allow improved manipulation by the various control schemes, such as the amount of reflux returned to the column, thereby allowing control of the distillation column to minimize the effect of disturbances to that achievable with continuous measurement.

Referring to FIG. 5, an ethylene/ethane feed stream (401) was provided to the distillation column (402). The fast GC (403) was employed to analyze the composition at intermediate tray locations in the column. The sample tap used for control was placed approximately one-third of the way down from the top of the column. A homogeneous, representative, single phase sample was obtained from the column and feed stream and sent to the fast GC in a timely manner. The compositional analysis provided by the fast GC is used to control the reflux ratio (defined as 406 divided by 404) of the column. The set point on the internal fast GC control loop is reset by a slower, outer control loop whose set point is controlled by a conventional chromatographic analysis. The flow rate of the bottoms (405), primarily ethane, is set equal to the flow rate of the ethane in the feed based upon the compositional analysis of the feed stream. The bottoms flow is then trimmed by the composition measured in the bottoms stream.

A second control scheme has been employed where the fast GC analyses at several intermediate tray locations, some conventional analyses, and various physical measurements have been supplied as inputs to a multivariable controller to achieve optimum column control.

Those with skill in the art will readily appreciate that various physical measurements (flow, temperature, pressure and the like) were also measured and used in both control schemes. While in this Example, the fast GC was used to control the reflux ratio of the column, the fast GC analysis of the column could also be used in other control schemes.

EXAMPLE 4

Figure 6:
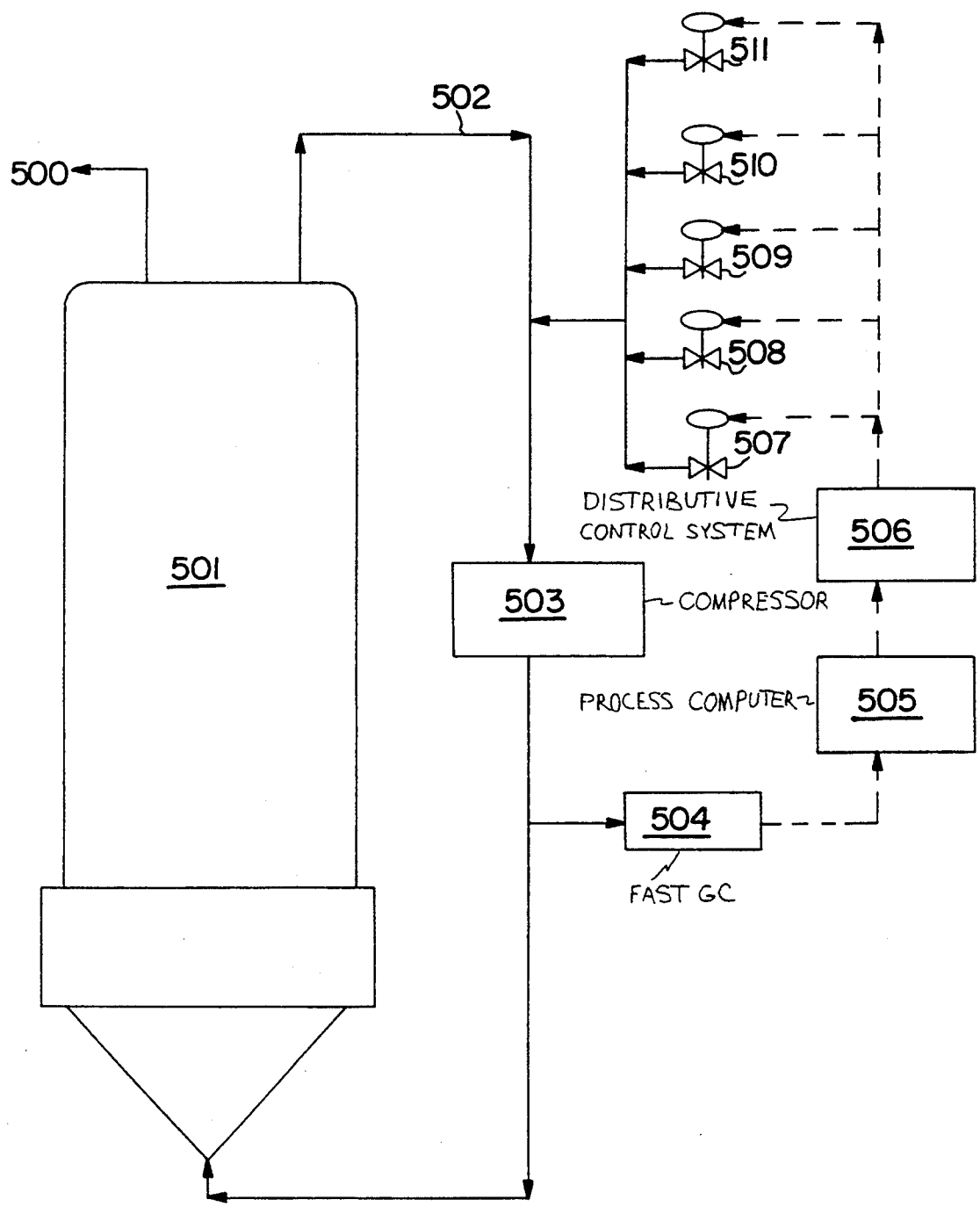
FIG. 6 is a diagram of a gas phase fluidized bed polyolefins reactor employing fast gas chromatography in the process control of the reactor.

A pilot plant scale gas phase fluidized bed polyolefins reactor (70 ft$^3$) was equipped with a fast GC. This reactor is well known to those with ordinary skill in the art and is employed to manufacture a wide range of polymers such as polyethylene, polypropylene and various copolymers. Referring to FIG. 6, the reactor (501) was equipped with a vent (500) and a recycle line (502), leading to a compressor (503) which recycles reactor gases back to the reactor. In this example, the reactor is used to manufacture polyethylene and the respective control valves controlled the flow rate of $C_2$ such as ethylene (507), $C_3$ such as propylene (508), $C_4$ such as butene (509), $C_6$ such as hexene (510) and hydrogen (511). A fast GC (504), using the fast temperature programming module described in Example 1, was employed to analyze the composition of the recycle gas stream. The output of the fast GC was sent to a process computer (505) which will be used to calculate the desired component feed rate set points. The desired feed rate set points are in turn sent to a distributive control system (506) which in turn is used to control the feed rate of the various components to the reactor.

The fast GC was constructed out of an old Union Carbide Model CM-7 oven. A fast electrometer, valve switching capabilities, and an old Varian flame ionization detector were added to the oven box along with the necessary regulators and gauges to control the flow of purge, carder and detector gases. A fast temperature programming module was also required for this measurement and was installed in the oven box. Instrumental parameters were was follows:

Instrument: Union Carbide Model CM-7 oven which is equipped with a Valco Model VIII 0.5 μL internal volume injection valve with low dead volume fittings, a flame ionization detector modified for high speed use, and a fast temperature programming module. Data acquisition and processing is accomplished with a Zeos 33 MHz 80486 computer equipped with 4 Megabytes of memory and a 130 Megabyte hard drive with Super-VGA display.

Columns: 10 m×0.32 mm I.D. $Al_2O_3$/KCl fused-silica capillary PLOT column with a 5 μm stationary phase thickness (Chrompack Part #7515 (50 m in length))

Oven Temperature: 110° C.

Column Temperature:
i) Hold at 90° C. for 10 seconds
ii) Program from 90° C. to 180° C. at 6° C./second,
iii) Hold at 180° C. for 25 seconds Injection System: Valco Model VIII 0.5 μL internal volume injection valve equipped with low dead volume fittings (Valco Part #AN-600E or #AN-700E).

Sample Volume: 0.5 μL

Detector: Flame Ionization that has been modified for high speed/capillary column analysis by minimizing dead volume and incorporating high speed signal amplification.

Carrier Gas: Hydrogen at a flow rate of approximately 13 mL/min (column head pressure is approximately 8 psig)

Detector Gases: Hydrogen at 30 mL/min Air at 350 mL/min

Cycle Time: 60 seconds

The control scheme of the reactor was programmed to control the $C_2$ partial pressure and to control the $X/C_2$ mole ratios (where $X=H_2$, $C_3$, $C_4$, $C_6$) based upon the analysis of the recycle gas stream. Time required to make the conventional GC analysis of the recycle gas stream is about 6–7 minutes (the 6–7 minute cycle time is presently used in closed loop control of the process). The time required to complete the separation and analysis of the gas stream and to reinitiate the cycle using the fast GC is approximately 1 minute. Based on models and simulation results, improved reactor performance (manifested in the form of reduced variability in reactor conditions) is expected when the process control scheme can be improved. These improvements can be due to modifications to the process dynamics, the process control and/or the analytical sampling needs of the UNIPOL TM process. Relatively simple process dynamics and effective controls make the analyzer sampling time the limiting factor in improved process control. With the addition of the fast GC, further reduction to the analyzer cycle time is expected to reduce the variance of gas composition from the set point by a total of about 93% when the analyzer sampling time is reduced from 6–7 minutes to about 1 minute. The reduction in deviation in process control will correlate to less off-specification product, fewer process upsets and enhanced reactor control.

We claim:

1. Gas chromatographic apparatus for rapidly analyzing samples in an industrial process, said apparatus operable to rapidly detect samples, the apparatus containing an injecting means, which feeds a chromatography column, the eluting samples from the column are provided to a detecting means which converts the samples into an electrical signal, said apparatus comprising:
   a) at least one gas chromatography column capable of separating components in a gas sample, having a sample inlet port located at an upstream portion of said column and a sample elution port at an outlet of said column;
   b) means for automatically selecting a sample to be analyzed;
   c) a valve for rapidly injecting into said chromatographic column a gas mixture that has a reproducible plug flow time of less than about 50 milliseconds;
   d) means for detecting said separated gas components from the outlet of the column and creating an electrical signal;
   e) means for converting said electrical signal to a digital signal at a rate of greater than 500 points per second;
   f) means for identifying sample components and calculating sample component levels from said digital signal;
   g) means for transferring said sample component identification and sample component level information to a process control computer; and
   h) means for reiterating the analysis wherein means e, f, and g are capable of being operated concurrently.

2. The apparatus of claim 1 wherein means for heating and cooling the chromatographic column and its contents at least 1° C. per second is provided.

3. The apparatus of claim 2 wherein the means for heating the chromatographic column and its contents is variable.

4. The apparatus of claim 2 wherein the means for heating the chromatographic column and its contents comprises an electrified conductive element.

5. A process for controlling the operation of industrial process equipment through the use of repetitive gas chromatography comprising:
   a) providing a controlled flow of carrier gas;
   b) providing an automated sample selection mechanism;
   c) providing an automated sample injection mechanism;
   d) automatically selecting the desired sample;
   e) injecting a sample of gas into a gas chromatographic column to be analyzed such that the plug flow time of the gas sample is reproducibly less than 50 milliseconds;
   f) separating the components of the gas sample by gas chromatography;
   g) detecting the separated components and their concentrations of said gas sample thereby creating an electrical signal;
   h) digitizing and amplifying the signal from said detector at the rate of at least 500 points per second;
   i) converting the digitized signal into component identification and concentrations;
   j) transferring the component identification and concentration to a process control computer; and
   k) providing a means for reinitiating the analysis process.

6. The process of claim 5 wherein the digitized signal is converted at a rate of from about 1000 to about 2000 points per second.

7. The process of claim 5 wherein the sample gas has a plug flow time of less than 25 milliseconds.

* * * * *

UNITED STATES PATENT AND TRADEMARK OFFICE
CERTIFICATE OF CORRECTION

PATENT NO. : 5,437,179

DATED : August 1, 1995

INVENTOR(S) : Wiegand et al.

It is certified that error appears in the above-identified patent and that said Letters Patent is hereby corrected as shown below:

Item [75],
Title page, under "Inventors", "John R. Parris" should read --John R. Parrish--.

Column 2, line 46, "carder" should read --carrier--.
Column 4, line 27, "carder" should read --carrier--.
Column 4, line 55, "carder" should read --carrier--.
Column 5, line 4, "carder" should read --carrier--.
Column 5, line 9, "carder" should read --carrier--.
Column 5, line 32, "carder" should read --carrier--.
Column 6, line 26, "carder" should read --carrier--.
Column 6, line 31, "carder" should read --carrier--.
Column 6, line 60, "was" should read --is--.
Column 11, line 38, after "device" insert --.--.
Column 11, line 65, "carder" should read --carrier--.
Column 11, line 66, "carder" should read --carrier--.
Column 13, line 32, "systems" should read --system--.
Column 14, line 47, "carder" should read --carrier--.
Column 18, line 4, "carder" should read --carrier--.

Signed and Sealed this

Ninth Day of April, 1996

Attest:

*Attesting Officer*

BRUCE LEHMAN

*Commissioner of Patents and Trademarks*